(12) United States Patent
Lipson et al.

(10) Patent No.: US 9,376,363 B2
(45) Date of Patent: Jun. 28, 2016

(54) METHOD FOR INHIBITING THE OXIDATION OF VO(ACAC)2 IN SOLUTION

(75) Inventors: Robert Lipson, London (CA); Cheng Lu, London (CA)

(73) Assignee: THE UNIVERSITY OF WESTERN ONTARIO, London, Ontario (CA)

( * ) Notice: Subject to any disclaimer, the term of this patent is extended or adjusted under 35 U.S.C. 154(b) by 1470 days.

(21) Appl. No.: 13/123,694

(22) PCT Filed: Oct. 20, 2009

(86) PCT No.: PCT/CA2009/001494
§ 371 (c)(1),
(2), (4) Date: Oct. 17, 2011

(87) PCT Pub. No.: WO2010/045719
PCT Pub. Date: Apr. 29, 2010

(65) Prior Publication Data
US 2012/0040192 A1    Feb. 16, 2012

Related U.S. Application Data

(60) Provisional application No. 61/136,990, filed on Oct. 20, 2008.

(51) Int. Cl.
| | |
|---|---|
| C09D 5/24 | (2006.01) |
| H01B 1/08 | (2006.01) |
| C07C 45/77 | (2006.01) |
| H01B 1/02 | (2006.01) |
| C01G 31/02 | (2006.01) |
| C07C 45/86 | (2006.01) |
| C09K 9/00 | (2006.01) |
| C09K 15/06 | (2006.01) |

(52) U.S. Cl.
CPC ............. *C07C 45/77* (2013.01); *C01G 31/02* (2013.01); *C07C 45/86* (2013.01); *C09K 9/00* (2013.01); *C09K 15/06* (2013.01); *H01B 1/02* (2013.01); *C01P 2002/52* (2013.01); *C01P 2002/72* (2013.01); *Y10T 428/31721* (2015.04)

(58) Field of Classification Search
CPC .............. H01B 1/00; H01B 1/08; H01B 1/14; H01B 1/20; H01B 1/22; C09D 5/24; C09D 5/082
See application file for complete search history.

(56) References Cited

U.S. PATENT DOCUMENTS

2013/0289317 A1*  10/2013  Siewert et al. ................ 568/826

OTHER PUBLICATIONS

Gibson, Susan E. "Transition Metals in Organic Synthesis—A Practical Approach" pp. 10-11 (1997).*

(Continued)

*Primary Examiner* — Mark Kopec

(57) ABSTRACT

The present invention provides a method to effectively inhibit the oxidization of $VO(acac)_2$ in solution for months. It is believed that $VO(acac)_2$ forms a π-complex with as many as three allylic alcohols which precludes reaction with any oxygen in the system. Although saturated and homo-allylic alcohols were also tested, this effect appears only in the allylic-alcohol based solutions. This ability to inhibit oxidation of $VO(acac)_2$ allows these solutions to be used for making thermochromic $VO_2$ film much more easily and economically as it avoids the requirement of operating under low oxygen level conditions. Thus the present invention provides a method of stabilizing vanadium oxyacetylacetonate ($VO(acac)_2$) in solution against oxidation for extended periods of time, comprising the steps of mixing the oxyacetylacetonate precursor in an allylic alcohol prior to spin-coating for $VO_2$ film formation. The allylic alcohol may be β-methallyl alcohol. Alternatively, the allylic alcohol may be any one of 4-buten-2-ol, 2-buten-1-ol, 1-penten-3-ol, 2-hexen-1-ol and 1-hexen-3-ol.

11 Claims, 4 Drawing Sheets

(56) References Cited

OTHER PUBLICATIONS

Sharpess K.B. et al; "High Stero-and Regioselectivities in the Transition Metal Catalyzed Epoxidations of Olefinic Alcohols by tert-Butyl Hydroperoxide" J. Am.Chem. Soc. May 9, 1973, vol. 95(18), pp. 6136-6137, chart I, 6136 right column.

Pan M. et al; "Properties of VO2 thin film prepared with precursors Vo(acac)2"; J. Cryst. Growth, 2004, vol. 265, pp. 121-126.

Grybos R. et al; "Kinetics of oxidation of vanadyl acetylacetonate by oxygen in methanolic solution"; Transition Met. Chem.; 1997, vol. 22, pp. 61-64.

* cited by examiner

METHOD FOR INHIBITING THE OXIDATION OF VO(ACAC)2 IN SOLUTION

CROSS REFERENCE TO RELATED FOREIGN PATENT APPLICATION

This application is a National Phase application claiming the benefit of PCT/CA2009/001494 filed on Oct. 20, 2009, in English; which further claims the benefit of priority from U.S. Provisional patent application Ser. No. 61/136,990 filed on Oct. 20, 2008, entitled METHOD FOR INHIBITING THE OXIDIZATION OF VO(ACAC)$_2$ IN SOLUTION, which was filed in English, both of which are incorporated herein by reference in their entirety.

FIELD OF THE INVENTION

The present invention relates to a method to effectively inhibit the oxidization of VO(acac)$_2$ in solution for extended periods of time, and more particularly the present invention relates to a stabilized composition of vanadium oxyacetylacetonate (VO(acac)$_2$) in an allylic alcohol and preparation of thermochromic films based on VO$_2$ synthesized from the stabilized compositions.

BACKGROUND OF THE INVENTION

Vanadium (IV) dioxide, VO$_2$, has been a subject of intense scrutiny because it undergoes a reversible semiconductor-to-metal phase transition at a relatively low temperature (68° C.) (see references 1, 2 and 3). This leads to dramatic changes in its electrical and optical properties in the near infrared (IR) (see references 4 and 5) that make it a useful material in several applications including smart windows, sensors, and optical storage devices (see reference 6). In addition to being a thermochromic material VO$_2$ is also electrochromic; that is, the phase transition can be induced by passing a current through the material by means of a voltage application.

Similarly, the phase transition can be induced by irradiating the sample with laser light provided the photon energy exceeds the band gap of the material (~0.6 eV; H. W. Verleur et al, Rev. Mod. Phys. 40, 737 (1968)). This makes VO$_2$ thin films appropriate for use as an optical limiter. Vanadium oxides can adopt many stoichiometries corresponding to different vanadium oxidation states. The preparation of stoichiometric VO$_2$ therefore requires stringent experimental control over the oxidation process in order to obtain the desired oxygen stoichiometry and crystallinity (see references 6 and 7). Pan et. al. showed that the sol-gel method can be easily used to fabricate VO$_2$ thin film from vanadium oxyacetylacetonate (VO(acac)$_2$) methanol solution (see reference 8). However, the inherent shortcoming to this method is the rapid oxidation of VO(acac)$_2$ in methanol solution (see reference 9). This drawback has impacted negatively on the economical development of thermochromic devices based on VO$_2$.

Therefore there is a need to provide a simple chemistry approach that stabilizes vanadium oxyacetylacetonate against oxidation in solution.

SUMMARY OF THE INVENTION

The present invention provides a method of stabilizing vanadium oxyacetylacetonate (VO(acac)$_2$) in solution against oxidation for extended periods of time, comprising the steps of mixing the oxyacetylacetonate precursor in an allylic alcohol prior to spin-coating for VO$_2$ film formation.

The allylic alcohol may be 3-methallyl alcohol. Alternatively, the allylic alcohol may be any one of 4-buten-2-ol, 2-buten-1-ol, 1-penten-3-ol, 2-hexen-1-ol and 1-hexen-3-ol.

The present invention also provides a composition of oxyacetylacetonate (VO(acac)$_2$) in solution stabilized against oxidation for extended periods of time, comprising vanadium oxyacetylacetonate (VO(acac)$_2$) dissolved in an allylic alcohol. The allylic alcohol may be β-methallyl alcohol.

The present invention also provides a thermochromic VO$_2$ film produced using the composition of oxyacetylacetonate (VO(acac)$_2$) dissolved in the allylic alcohol.

A further understanding of the functional and advantageous aspects of the invention can be realized by reference to the following detailed description and drawings.

BRIEF DESCRIPTION OF THE DRAWINGS

Preferred embodiments of the invention will now be described, by way of example only, with reference to the drawings, in which.

DETAILED DESCRIPTION OF THE INVENTION

Figure 1:
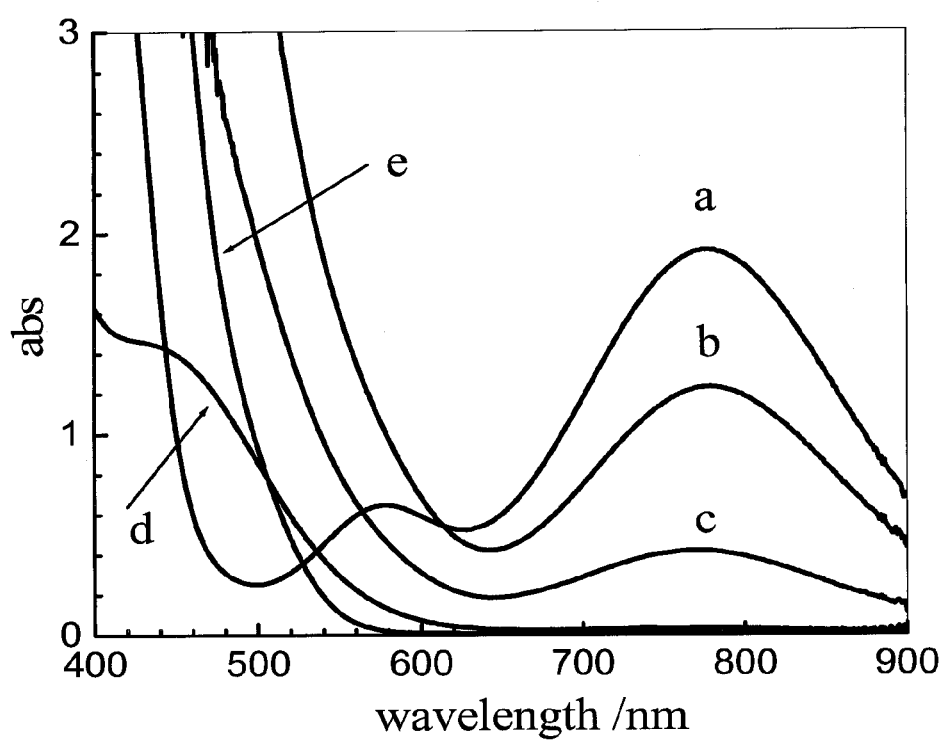
FIG. 1 shows the absorption spectra of VO(acac)$_2$ dissolved in methanol, (a) a fresh made solution, (b) a solution aged for 3 days, (c) a solution aged for 1 month, (d) a methanol solution saturated by O$_2$, (e) a solution of VO(i-C$_3$H$_7$O)$_3$ dissolved in methanol.

Generally speaking, the embodiments described herein are directed to a method to inhibit the oxidization of VO(acac)$_2$ in solution for extended periods of time. As required, embodiments of the present invention are disclosed herein. However, the disclosed embodiments are merely exemplary, and it should be understood that the invention may be embodied in many various and alternative forms.

The figures are not to scale and some features may be exaggerated or minimized to show details of particular elements while related elements may have been eliminated to prevent obscuring novel aspects. Therefore, specific structural and functional details disclosed herein are not to be interpreted as limiting but merely as a basis for the claims and as a representative basis for teaching one skilled in the art to variously employ the present invention. For purposes of teaching and not limitation, a method to inhibit the oxidization of VO(acac)$_2$ in solution for extended periods of time is disclosed herein.

As used herein, the terms "about", and "approximately" when used in conjunction with ranges of concentrations, temperatures or other physical or chemical properties or characteristics is meant to cover slight variations that may exist in the upper and lower limits of the ranges of properties/characteristics.

The VO(acac)$_2$ molecule has C$_{2v}$ geometry. Spectroscopic studies have shown that the vanadium atom is chemically accessible at the sixth position leading to the formation of adducts with different solvent molecules. The resultant octahedral complex is easily oxidized by atmospheric oxygen to vanadium (V) species in many solvents such as water and alcohols via a previously disclosed mechanism (see references 9 and 10).

Given the important role that solvation adducts play in the oxidation of VO(acac)$_2$, the inventors studied different solvents that could bind to VO(acac)$_2$ while at the same time inhibiting the oxidation of V(IV) to V(V). One very promising candidate in this regard are allylic alcohols which have C=C and —OH functional groups at α, β position respectively.

Experimental

The alcohols used during these experiments and listed in Table 1 can be categorized into three groups: saturated alcohols, allylic alcohols and homo-allylic alcohols. Each was commercially available with chemical reagent purity, and used as received. VO(acac)$_2$ was dissolved in each solvent to form 0.05 mol/L solutions. The oxidization of VO(acac)$_2$ leads to a distinct solution color change. Absorption spectra of the precursor solutions between 400 nm and 900 nm were recorded using a Cary 50 spectrometer having a wavelength resolution of 1 nm, and using methanol as a reference. Powder X-ray diffraction (XRD) data were collected using a Rigaku RU-200BVH rotating anode diffractometer employing a Co Kα source (λ=1.7892 Å).

TABLE 1

Alcohol solvents used to prepare VO(acac)$_2$ solution

| Saturated alcohol | Unsaturated alcohol | |
| --- | --- | --- |
| | Allylic alcohol | Homo-allylic alcohol |
| methanol | β-methallyl alcohol (BMA) | 1-buten-4-ol |
| ethanol | 4-buten-2-ol | 3-hexen-1-ol |
| iso-propanol | 2-buten-1-ol | 4-penten-2-ol |
| | 1-penten-3-ol | |
| | 2-hexen-1-ol | |
| | 1-hexen-3-ol | |

Results and Discussion

Figure 2:
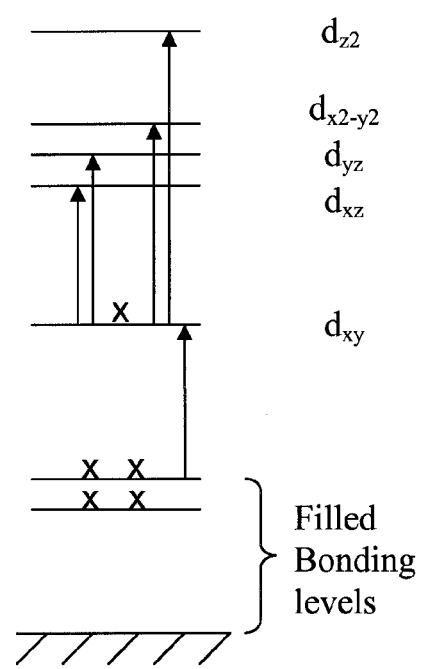
FIG. 2 shows an unscaled energy level scheme for vanadyl (IV) complex.

In FIG. 1 trace a is a visible-near infrared (IR) spectrum of a freshly prepared VO(acac)$_2$ methanol solution. The well-known energy level scheme for V(IV)O$^{2+}$ complexes (see references 11, 12, 13 and 14) reproduced in FIG. 2 allow the main features to be readily assigned. Specific d-d transitions involving the single V 3d electron come at ~780 nm ($d_{xy}, d_{yz}, d_{x^2-t_2} \leftarrow d_{xy}$) and ~570 nm ($d_{z^2} \leftarrow d_{xy}$). Each newly-prepared solution is blue-colored but these maxima shift slightly in different solvents due to the adduct formation. There are also intense charge-transfer absorption bands, due primarily to electron transfer from orbitals located primarily on the vanadyl oxygen to orbitals primarily located on V, in the near UV (<500 nm) (see references 11 and 13) which were not recorded to allow the longer wavelength visible-near IR features to be shown on scale.

The color of VO(acac)$_2$/methanol solution standing in air was found to gradually change from blue to green to yellow and finally to orange over several days which is attributed to the oxidation of V(IV) to V(V). In FIG. 1 (traces a-c) clearly shows these changes spectroscopically. The d-d transition bands at 780 nm and 570 nm decrease in intensity while the strong first charge transition band persists, although a distinct red shift is observed over time. The disappearance of the d-d bands indicates that oxidation process involves the lone 3d electron on vanadium. The red shift in the charge transfer band over time is expected because the repulsion experienced by the ligand electron with the half-filled 3d orbital on the V is removed by the oxidation step (see reference 13). The solution turned orange immediately if it was initially saturated with O$_2$ gas (FIG. 1 trace d) which confirms that O$_2$ from the atmosphere is the oxidant involved. This spectrum strongly resembles that obtained for a V(V)O(i-OPr)$_3$/methanol solution (FIG. 1 trace e).

Similar spectra were recorded using other saturated alcohols such as ethanol and i-propanol, which strongly suggests that this class of alcohol cannot inhibit the oxidation of VO(acac)$_2$.

Allylic alcohols were then examined. β-methallyl alcohol (BMA, 2-methyl-2-propen-1-ol) is described here as a typical example. Similar results were found for the other allylic alcohols listed in Table 1.

Figure 3:
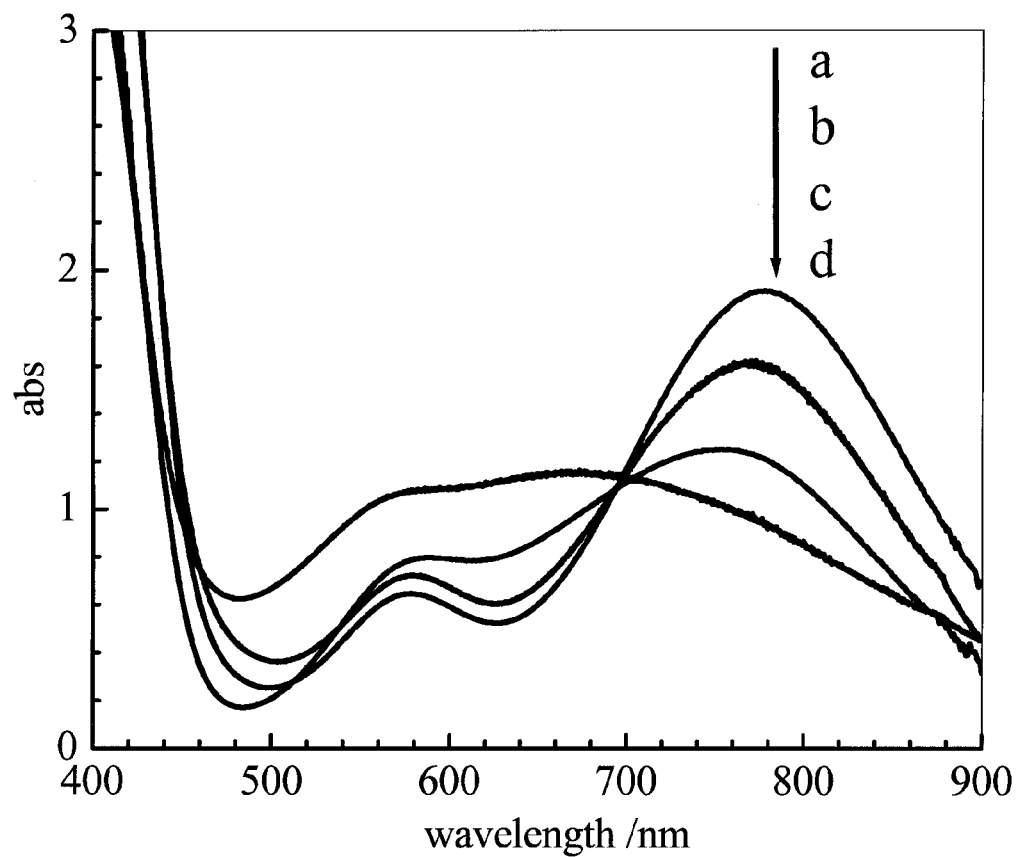
FIG. 3 shows the absorption spectra of VO(acac)$_2$ dissolved in β-methallyl alcohol (BMA) at different time intervals, (a) a freshly made solution, (b) a solution aged 3 days, (c) a solution aged 1 month, and (d) a solution aged 6 months.

A VO(acac)$_2$/BMA solution was found to retain its original blue color for months. FIG. 3 shows its absorption spectrum at different time. Not surprisingly, the absorption spectrum of a freshly made solution resembles that obtained for a freshly made VO(acac)$_2$/methanol solution. The spectra in FIG. 3 confirm that the d-d transitions persist over time although the long wavelength band was found to continuously shift to the blue while the near-UV first charge transfer band exhibited no change in wavelength. In addition, the intensity of the peak centered at 780 nm ($d_{xy}, d_{yz}, d_{x^2-t_2} \leftarrow d_{xy}$) decreased while the peak centered at 570 nm ($d_{z^2} \leftarrow d_{xy}$) increased. After 6 months, the peaks became overlapped and solution exhibited a darker blue color. There also appears to be an isosbetic point near 700 nm that suggests that over time a second species forms most likely by an additional ligand exchange. However, the vanadium center does not become oxidized.

The similarity of the VO(acac)$_2$/methanol and VO(acac)$_2$/BMA solutions suggests that ligation of a solvent molecule at the open position of the VO(acac)$_2$ molecule does not have profound effect on the energy levels. The VO(acac)$_2$ is readily oxidized in methanol presumably because an O$_2$ molecule can displace the alcohol from the coordination sphere. The fact that the vanadium complex is resistant to oxidation by O$_2$ in allylic alcohols indicates that not only is the oxygen of the hydroxyl moiety involved in coordination to the central vanadium atom, but also the π-system of the β-unsaturated bond. One possible structure is of the form:

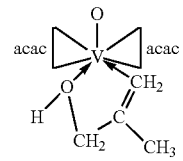

Without being bound by any theory or theorem, it is believed that the unsaturated double bond of an allylic alcohol can function as electron donor in the Pd(II)/alyllic alcohol system. Inhibition of oxidation was not found for the homo-allylic alcohols, which may be due to additional methylene group in these compounds which makes it sterically difficult for the alcohol to act in a bidentate fashion.

Stabilized solutions of the allylic alcohol were obtained with concentrations of vanadium oxyacetylacetonate (VO(acac)$_2$) in the allylic alcohol spanning a range over which the vanadium oxyacetylacetonate is soluble in the allylic alcohol.

Figure 4:
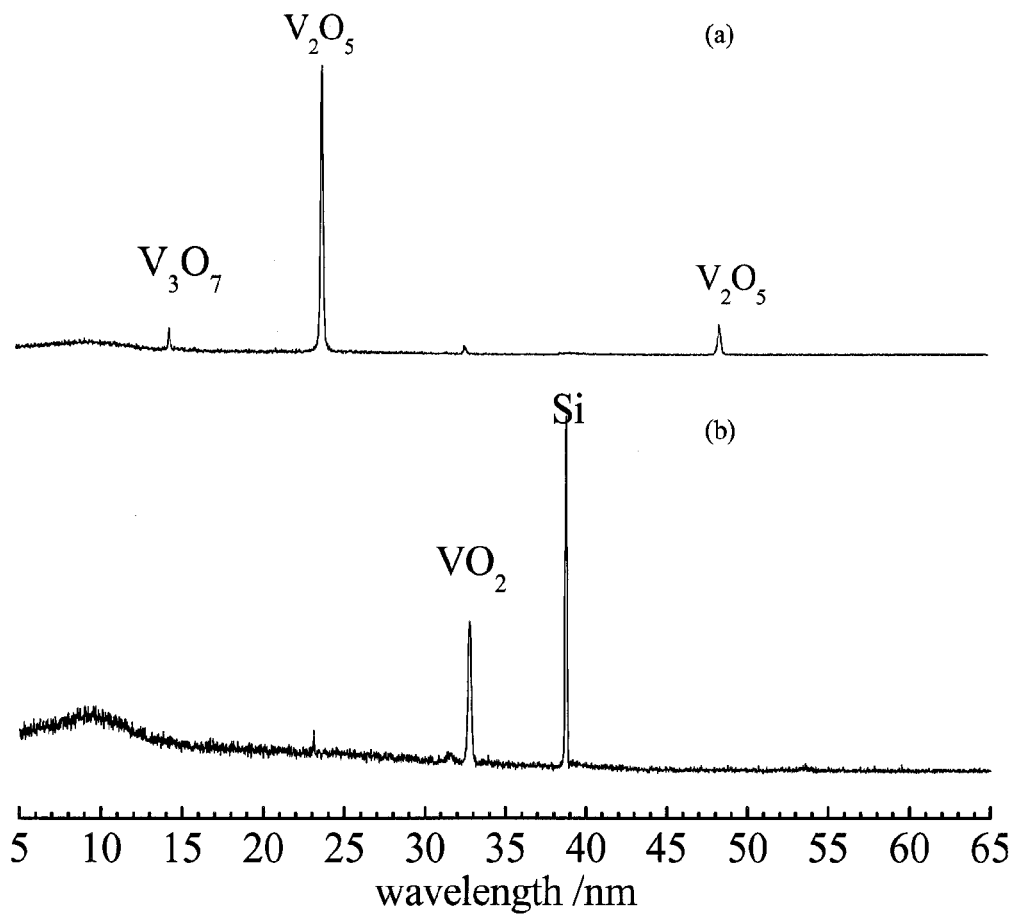
FIG. 4 shows x-ray diffraction (XRD) spectra of thin films made from the VO(acac)$_2$ solutions aged for 3 days, (a) a VO(acac)$_2$/methanol solution, (b) a VO(acac)$_2$/BMA solution; the diffraction peak assignments are labeled.

Thin films of VO$_2$ made from VO(acac)$_2$ methanol and BMA solutions (3 days aged) were obtained by spin casting onto and baking at 600° C. under an Ar environment. The XRD profiles (FIG. 4) clearly reveal the differences in chemical identities of the species in the film: oxidized species such as $V_2O_5$ and $V_3O_7$ are present in films prepared from methanol-based precursor solutions, while mainly the $VO_2$ phase is formed when using BMA solutions. These results confirm that the allylic alcohol prevents $VO(acac)_2$ from being oxidized.

In an exemplary, non-limiting example, the process of spin coating was used to fabricate thin films of $VO_2$ from the precursor solutions described in this work. A typical spin coating process comprises four steps: dispensing, accelerating, spin coating and drying.

In general, a small drop of the precursor solution is deposited on or near the center of a substrate while a supporting stage is rotated at a low angular speed of ~500 rpm. This spreads the fluid evenly over the substrate. The substrate is then spun at a much higher rotation speed (1000-4000 rpm). Finally, the coated sample is placed into a convection oven maintained at ~100° C. to evaporate any remaining solvent. This effectively solidifies the coating in place. The $VO_2$ films were formed by heating the sample between 500-650° C. under 10 Torr partial pressure of oxygen. Using lower pressures and longer heating times yielded $VO_2$ films with better crystallinity.

The film thickness and other properties depend on the nature of the gel (viscosity, concentration, surface tension, etc.) and the parameters chosen for spin coating and processing. The solution concentration, spinning speed and time need to be adjusted to obtain different film thicknesses. Overall, the spin coating procedure is simple and repeatable.

It will be appreciated that any liquid based film deposition technique may be used to deposit thermochromic $VO_2$ films using the stabilized vanadium oxyacetylacetonate ($VO(acac)_2$) solutions disclosed herein. Non-limiting examples include spin coating, screen printing, evaporation and spraying to mention just a few.

In summary, the method disclosed herein provides a very economical and simple effective method for effectively inhibiting the oxidization of $VO(acac)_2$ in solution for extended periods of time. The choice of solvent for the sol-gel synthesis of $VO_2$ thin films has a profound effect on the oxidation of $VO(acac)_2$ precursor in solution. Specifically, unlike solutions made with saturated and homo-allylic alcohols which oxidize within days, allylic alcohols effectively inhibit the oxidation of $VO(acac)_2$ for as long as six months. It is postulated that allylic alcohols are effective bidentate ligands which are not readily displaced by $O_2$ in solution thereby protecting the V(IV) metal center. This discovery will relax the chemical imperative to form $VO_2$ immediately after making up a precursor solution for a sol-gel synthesis. The method and results disclosed herein permits $VO_2$ thin films to be made easily and reproducibly, and the quality of the $VO_2$ thin films formed is excellent. Since this material exhibits a low-temperature semiconductor-to-metal phase transition it will be appreciated that many devices based on $VO_2$ can now be more easily realized.

It will be appreciated that while the above description has disclosed making pure $VO_2$ thin films to be made easily and reproducibly, it will be appreciated that doped $VO_2$ thin films can also be made with the purpose of the doping being to vary or tune the semiconductor-to-metal phase transition temperature. Various dopants that can be used include $Al^{3+}$ (Chen et al. Solar Energy Materials and Solar Cells, 93, 1550 (2009)), $W^{6+}$ (R. Binions et al, Surface Coatings and Technologies 201, 9368 (2007)), $Mo^{6+}$ (X. Shi-Qeng et al, Chinese Phys. Lett. 20, 148 (2003)), and $Nb^{5+}$ (C. Piccirillo et al, Eur. J. Inorg. Chem. 25, 4050 (2007)), among others. Previous work has shown that low-valent cations (such as $Al^{3+}$ and $Cr^{3+}$) tend to raise the semiconductor-to-metal phase transition while high-valent cations ($Nb^{6+}$, $W^{6+}$, and $Mo^{6+}$) have the opposite effect. This rule of thumb however is highly dependent on the concentration of cations. For example, adding 10% $Al^{3+}$ by content has been found to drop the phase transition down to ~40° C.

The thermochromic $VO_2$ films may be deposited on many types of substrate including crystalline solids, polymers and amorphous solids. The crystalline solids may be semiconductors, semimetals or metals. The substrate may be glass, silicon, quartz, and sapphire, polymers, and their chemically modified analogs. For example, the substrate may be a polyimide polymer with a high glass transition temperature. It will be understood the present invention is not restricted to using these substrates, they are meant to be non-limiting examples.

The thermochromic $VO_2$ film may be coupled to means for inducing a semi-conductor to metal transition in the thermochromic $VO_2$ film. For example, the means for inducing a semi-conductor to metal transition in the thermochromic $VO_2$ film includes any one or combination of a temperature controller coupled to heater elements coupled to said substrate or said thermochromic $VO_2$ film, a voltage controller electrically coupled to said thermochromic $VO_2$ film for resistive heating of the thermochromic $VO_2$ film or resistive heating of a resistive heater film on the substrate, and a laser source for irradiating the thermochromic $VO_2$ film for radiative heating of the thermochromic $VO_2$.

As used herein, the terms "comprises", "comprising", "includes" and "including" are to be construed as being inclusive and open ended, and not exclusive. Specifically, when used in this specification including claims, the terms "comprises", "comprising", "includes" and "including" and variations thereof mean the specified features, steps or components are included. These terms are not to be interpreted to exclude the presence of other features, steps or components.

The foregoing description of the preferred embodiments of the invention has been presented to illustrate the principles of the invention and not to limit the invention to the particular embodiment illustrated. It is intended that the scope of the invention be defined by all of the embodiments encompassed within the following claims and their equivalents.

REFERENCES

1. Morin, F. J., Oxides Which Show a Metal-to-Insulator Transition at the Neel Temperature. *Phys. Rev. Lett.* 1959, 3, 34.
2. Tuchkevich, V. M.; Frenkel, V. Y., *Semiconductor Physics*. Consultants Bureau, New York, 1986
3. Biermann, S.; Poteryaev, A.; Lichtenstein, A. I.; Georges, A., Dynamical Singlets and Correlation-Assisted Peierls Transition in $VO_2$. *Phys. Rev. Lett.* 2005, 94, 026404-026404.
4. Manning, T. D.; Parkin, I. P.; Clark, R. J. H.; Sheel, D.; Pemble, M. E.; Vernadou, D., Intelligent window coatings: atmospheric pressure chemical vapour deposition of vanadium oxides. *J. Mater. Chem.* 2002, 12, 2936-2939
5. Lu, S.; Hou, L.; Gan, F., Surface analysis and phase transition of gel-derived $VO_2$ thin films. *Thin Solid Films* 1999, 353, 40-44
6. Gurvitch, M.; Luryi, S.; Polyakov, A.; Shabalov, A.; Dudley, M.; Wang, G.; Ge, S.; Yakovlev, V., $VO_2$ films with strong semiconductor to metal phase transition prepared by the precursor oxidation process. *J. Appl. Phys.* 2007, 102, 033504-033513

7. Yuan, N.; Li, J.; Lin, C., Valence reduction process from sol-gel V$_2$O$_5$ to VO$_2$ thin films. *Appl. Surf. Sci.* 2002, 191, 176-180.
8. Pan, M.; Zhong, H.; Wang, S.; Liu, J.; Li, Z.; Chen, X.; Lu, W., Properties of VO$_2$ thin film prepared with precursor VO(acac)$_2$. *J. Cryst. Growth* 2004, 265, 121-126.
9. Grybo, R.; Samotus, A.; Popova, N.; Bogolitsyn, K., Kinetics of oxidation of vanadyl acetylacetonate by oxygen in methanolic solution. *Transition Met. Chem.* 1997, 22, 61-64.
10. Datsko, O. R.; Belousov, V. M.; Fedevich, E. V., Liquid phase oxidation of allyl alcohol by air oxygen in acetic acid medium. *React. Kinet. Catal. Lett.* 1982, 19, 255-258
11. Ballhausen, C. J.; Gray, H. B., The Electronic Structure of the Vanadyl Ion. *Inorg. Chem.* 1962, 1, 111-122.
12. Selbin, J.; Holmes, L. H.; McGlynn, S. P., Electronic structure, spectra and magnetic properties of oxycations—IV ligation effects on the infra-red spectrum of the vanadyl ion. *J. Inorg. Nucl. Chem.* 1963, 25, 1359-1369.
13. Ortolano, T. R.; Selbin, J.; McGlynn, S. P., Electronic Structure, Spectra, and Magnetic Properties of Oxycations. V. The Electronic Spectra of Some Vanadyl Complexes. *J. Chem. Phys.* 1964, 41, 262-268.
14. Selbin, J.; Morpurgo, L., Spectral studies of low symmetry oxovanadium(IV) complexes. *J. Inorg. Nucl. Chem.* 1965, 27, 673-678.

Therefore what is claimed is:

1. A method of stabilizing vanadium oxyacetylacetonate (VO(acac)$_2$) in solution, comprising the steps of inhibiting oxidation of vanadium oxyacetylacetonate by mixing the vanadium oxyacetylacetonate with an oxidation inhibitor and dopant metal ions to form a solution stabilized against oxidation, wherein the oxidation inhibitor is an allylic alcohol.

2. The method according to claim 1 wherein said allylic alcohol is β-methallyl alcohol.

3. The method according to claim 1 wherein said allylic alcohol is selected from the group consisting of 4-buten-2-ol, 2-buten-1-ol, 1-penten-3-ol, 2-hexen-1-ol and 1-hexen-3-ol.

4. The method according to claim 1 wherein the steps of inhibiting oxidation includes dissolving said vanadium oxyacetylacetonate (VO(acac)$_2$) in said allylic alcohol.

5. The method according to claim 4 wherein said allylic alcohol is β-methallyl alcohol.

6. The method according to claim 4 wherein said allylic alcohol is selected from the group consisting of 4-buten-2-ol, 2-buten-1-ol, 1-penten-3-ol, 2-hexen-1-ol and 1-hexen-3-ol.

7. The method according to claim 1 wherein said dopant metal ions are selected from the group consisting of W$^{6+}$, Mo$^{6+}$, Nb$^{5+}$ Al$^{3+}$ and Cr$^3$.

8. The method according to claim 1, and wherein the stabilized solution is a thermochromic VO$_2$ film composition.

9. The method according to claim 1, including steps of stabilizing the vanadium oxyacetylacetonate (VO(acac)$_2$) in solution for at least a day.

10. A composition, comprising vanadium oxyacetylacetonate (VO(acac)$_2$) dissolved in an oxidation inhibitor, wherein the oxidation inhibitor is an allylic alcohol such that the composition is stabilized against oxidation and wherein the composition further comprises dopant metal ions.

11. The composition according to claim 10, wherein a concentration of said vanadium oxyacetylacetonate (VO(acac)$_2$) in said allylic alcohol spans a range over which said vanadium oxyacetylacetonate is soluble in said allylic alcohol.

* * * * *